United States Patent [19]
Carpenter et al.

[11] Patent Number: 4,806,343
[45] Date of Patent: Feb. 21, 1989

[54] CRYOGENIC PROTECTANT FOR PROTEINS

[75] Inventors: John F. Carpenter, Davis, Calif.; Steven C. Hand, Lafayette, La.; John H. Crowe; Lois M. Crowe, both of Davis, Calif.

[73] Assignee: University of Southwestern Louisiana, Lafayette, La.

[21] Appl. No.: 839,330

[22] Filed: Mar. 13, 1986

[51] Int. Cl.$^4$ .................. A61K 37/22; A61K 9/64; A61K 31/40; B01J 13/02

[52] U.S. Cl. .................................. 424/450; 34/5; 264/4.3; 424/94.3; 428/402.2; 435/188; 436/829; 514/1; 514/3; 514/6; 514/779; 514/971

[58] Field of Search .............. 264/4.3; 427/213.3; 428/402.2; 424/94, 450, 94.3; 514/1, 777, 971, 6; 436/829; 34/5; 435/188

[56] References Cited

U.S. PATENT DOCUMENTS

| | | | |
|---|---|---|---|
| 3,124,517 | 3/1964 | Eloy | 424/94 X |
| 4,133,874 | 1/1979 | Miller et al. | 428/402.2 X |
| 4,169,012 | 9/1979 | Dawson et al. | 435/188 X |
| 4,229,360 | 10/1980 | Schneider et al. | 424/450 X |
| 4,247,411 | 1/1981 | Vanlerberghe et al. | 424/450 X |
| 4,411,894 | 10/1983 | Schrank et al. | 514/777 X |
| 4,439,181 | 3/1984 | Blackshear et al. | 514/3 X |

OTHER PUBLICATIONS

Yamazaki: "Function of Peroxidase as an Oxygen-Activating Enzyme", *Iron-Sulfur Proteins*, Edit. by Spiro, T. G., John Wiley & Sons, (1982), pp. 433–442.

Maret: "Methodology of Metal Exchange in Metalloproteins", *Zinc Enzymes*, Birkhauser Boston, Inc. (1986), pp. 17–25.

Bertini et al. "Metal Substitution as a Tool for the Investigation of Zinc Proteins", *Zinc Enzymes*, Birkhauser Bostin, Inc. (1986), pp. 27–47.

Crowe et al.: "Stabilization of Dry Phospholipid Bilayers and Proteins by Sugars" *Biochem. J.* (1987) vol. 242 (in Press).

Crowe et al.: "Interactions of Sugars with Membranes", *Biochimica et Biophysica Acta* (1988) (in Press).

Carpenter et al.: "Modes of Stabilization of a Protein by Organic Solutes During Desiccation", *Cryobiology*, vol. 25 (1988) (in Press).

Simpson, R. T. et al.: "Zinc and Cobalt Alkaline Phosphatases", (1969) *Ann. N.Y. Acad. Sci.* 166:670–695.

Little, C: "Metal Ion Substitution in Phospholipase C(Basillus Cereus) and its Effect on Enzyme Stability", (1982) *Int. J. Biol. Macromol.* 4:434–436.

Whittam et al.: "Effects of the Freeze-Thaw Process on Alpha Amylase", *Cryobiology* 10:240–243 (1973).

Chikama et al.: "Denaturation of Catalase by Freezing and Thawing", *Nature* 190:83–84 (1961).

Hanafusa: "Denaturation of Enzyme Protein by Freeze-Thawing and Freeze-Dry", *Freezing and Dry-*
(List continued on next page.)

*Primary Examiner*—Richard D. Lovering
*Attorney, Agent, or Firm*—Keaty & Keaty

[57] ABSTRACT

A method of protecting soluble proteins such that their biological activity is preserved after freezing by exposing the protein to a carbohydrate and transition metal ion prior to freezing. The protected protein can then be thawed or lyophilized and rehydrated without denaturation of impairment of the protein's biological activity. The protein is preferably exposed to the carbohydrate by placing it in a 25–100 mM aqueous solution of carbohydrate and 2 mM $Z^{+2}$. This method is especially effective in preserving the biological activity of fragile proteins such as the enzyme phosphofructokinase. The present method can be used to preserve pharmaceutically useful proteins in a frozen or freeze-dried form for storage and distribution. The treated protein can be thawed or rehydrated and administered directly to a user without removing the cryoprotectant since the carbohydrates and trace amounts of many transition metal ions are nontoxic.

4 Claims, 1 Drawing Sheet

OTHER PUBLICATIONS

*ing of Microorganisms,* ed by TokioNei (Univ. of Tokyo Press, Tokyo 1969), pp. 117–129.

Brandts et al.: "The Low Temperature Denaturation of Chymotrypsingen in Aqueous Solution and in Frozen Aqueous Solution", *The Frozen Cell,* (1970), pp. 189–212.

Pennell: "Low-Temperature Preservation of Proteins", Fed. Proc. 24(2); S 269–274 (1965).

Chilson et al.: "Effects of Freezing on Enzymes", Fed. Proc. 24(2); S55–65 (1965).

Hellman et al.: "The Effect of Freeze-Drying on the Quaternary Structure of L-Asparaginase from Erwinia Carotovora," *Biochimica et Biophysica Acta,* 749:133–142 (1983).

Carpenter et al.: "Cryoprotection of Phosphofructokinase with Organic Solutes . . ." *Archives of Biochemistry of Biophysics,* 250:505–512 (1986).

Carpenter et al.: "Stabilization of Phosphofructokinase with Sugars During Freeze-Drying . . .", *Biochimica et Biophysica Acta,* 923:109–115 (1987).

J. H. Crowe et al.: "Preservation of Membranes in Anhydrobiotic Organisms: The Role of Trehalose", *Science,* vol. 223, No. 4637, pp. 701–703, Feb. 17, 1984.

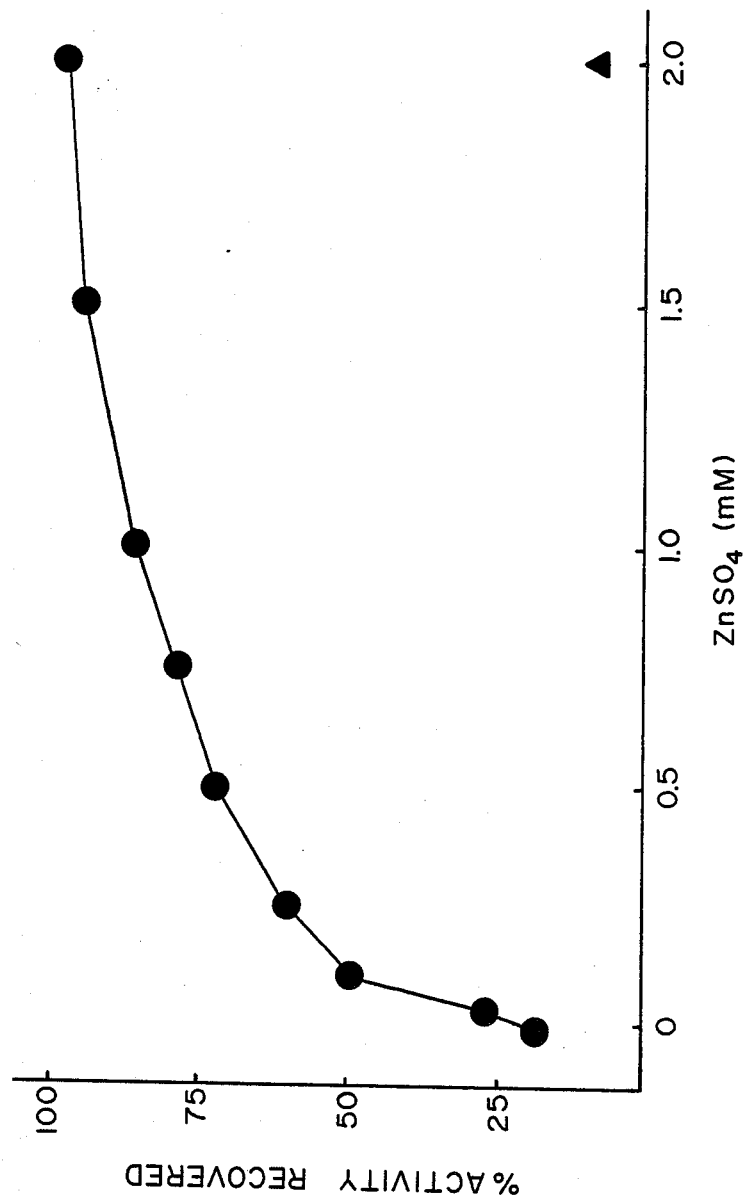

CRYOGENIC PROTECTANT FOR PROTEINS

BACKGROUND OF THE INVENTION

1. Field of the Invention

This invention concerns a method of protecting proteins such that their biological activity is preserved after freezing. This protection is achieved by adding a cryoprotectant that preserves biological activity of the protein in spite of freezing or lyophilization. More particularly, the invention concerns a method for preserving therapeutically effective proteins so that they can be conveniently stored in a nonliquid form while retaining substantially all of their biological activity.

2. General Discussion of the Background

Proteins are one of the almost universal constituents of living organisms. The fragility of living organisms and their usual ability to survive only within very narrow ranges of environmental conditions can be explained by a protein's loss of biological activity outside of a relatively narrow temperature range. For example, freezing often permanently changes the three dimensional tertiary structure of proteins, usually resulting in a loss of biological activity.

An especially sensitive kind of protein is an enzyme. Enzymes are polypeptide molecues that are produced by living cells and catalyze specific biochemical reactions at body temperatures. An example of such an enzyme is phosphofructokinase (PFK) which is a rate limiting catalyst in the glycolytic pathway. PFK catalyzes the addition of a phosphate group to fructose 6-phosphate, but once the enzyme is frozen it irreversibly loses all catalytic activity.

Since proteins play an important role in the function and regulation of living organisms, proteins have also become useful pharmaceutical agents. For example, the pancreatic protein insulin is instrumental in controlling animal blood sugar levels. If an animal's production of insulin is impaired, the resulting physiological condition is known as diabetes. This disease is usually treated by injecting specific doses of insulin into the animal. The cost and inconvenience of such treatment is increased, however, by the necessity of refrigerating the insulin in liquid form to preserve its biological activity until it is administered to a patient. Even at refrigeration temperatures, however, the protein is unstable and loses some of its activity. It would therefore be desirable to freeze such proteins to give them a longer shelf life.

It is not presently possible to simply freeze a protein such as insulin because freezing and subsequent thawing usually diminishes the biological activity of the protein. This problem has resulted in efforts to find ways to preserve the biological activity of proteins after they are frozen or lyophilized.

For example, U.S. Pat. No. 4,180,917 discloses a multistep process for freeze-drying enzymes in which the enzymes typically recover about 75 to 85% of their biological activity following freeze-drying. The method is complicated by the need for concentrating the enzyme solution using reverse osmosis or ultrafiltration and adding water insoluble salts. The protease and alpha-amylase compositions treated by this method are also quite stable to begin with and would retain a substantial amount of their activity after freezing even without addition of insoluble salts and reverse osmosis.

U.S. Pat. No. 3,607,858 describes a method of freeze-drying human blood proteins in the presence of small amounts of nonionic surface active agents with very rapid freezing in small containers. The globulins treated by this method are already quite stable to freezing and would survive freeze-drying even without addition of surface active agent. The addition of the nonionic surfactant simply serves to speed up the process of redissolving the globulin.

Although not dealing with preservation of proteins, U.S. Pat. No. 4,134,214 discloses that a polysaccharide antigen can be preserved by freeze-drying it at temperatures of $-20°$ to $-40°$ C.

Similarly unrelated to protein preservation is the work of Crowe et al. at the University of California-Davis with liposomes. A liposome is an artificial vesicle comprised of one or more concentric phospholipid bilayers. Crowe has shown, for example, in *Science*, vol. 223, pp. 701–703 (Feb. 17, 1984), that addition of trehalose alone to liposomes allows them to be freeze-dried and rehydrated without disruption of their phospholipid membranes. The mechanism of protection suggested by Crowe is a direct interaction between the phospholipid polar head groups and trehalose that prevents adhesion between the head groups during freezing. Crowe also believes that trehalose reduces the transition temperature of the liposomes and inhibits thermotropic gel to liquid crystalline phase transitions that are known to result in leakage of the contents of hydrated phospholipid vesicles.

The prior art had suggested that cryoprotectants such as dimethylsulfoxide (DMSO) and glycerol exerted protective action on proteins by altering the structure of the water solvent through a thermodynamic effect. Gekko et al., *Biochemistry* 20:4667–4676 (1981). It would therefore not be predicted that trehalose would protect proteins since Crowe had taught that the mechanism of trehalose action was one of direct interaction with the substance being protected.

The use of prior cryoprotectants, such as DMSO, with proteins present serious problems since DMSO and other cryoprotectants are biologically incompatible materials. If such an incompatible material were added to proteins, the cryoprotectant had to be removed prior to use of the protein in a biological system to prevent toxic reactions. If the incompatible material had reducing properties, it could also cause "protein browning" which diminishes or destroys the activity of the protein and turns it brown. This protein browning phenomenon is discussed in Lea, C. H. and R. S. Hannan, *Biochim. Biophys. Acta.*, 3:313 (1949); Lea, C. H. and R. S. Hannan, *Biochim. Biophys. Acta.*, 4:518 (1950); Lea, C. H. and R. S. Hannan, *Biochim. Biophys. Acta.*, 5:433 (1950); Lea, C. H. and R. S. Hannan, *Nature*, 165:438 (1950); Feeney, R. E., G. Blankenhorn and H. Dixon, *Adv. Prot. Chem.*, 29:135 (1975).

Another problem with prior art cryoprotectants such as DMSO and glycerol is that they must be present in solution in several molar amounts before they exert their cryoprotective influence. Such excessive amounts of an additive can disrupt biological function and are difficult to remove.

It is accordingly an object of this invention to provide a method of protecting proteins such that their biological activity is preserved after freezing.

Another object of the invention is to provide such a method of preservation which will protect the protein during freezing and thawing or during lyophilization and subsequent rehydration.

Yet another object of the invention is to provide such a method of preservation which employs only nontoxic, biologically compatible additives.

Still another object of the invention is to provide such a method that will permit proteins, such as therapeutically useful substances and enzymes, to be frozen and thawed or lyophilized and rehydrated while retaining the majority of their biological activity.

Even yet another object is to provide a cryogenic protectant additive for proteins which is nonreducing and does not cause protein browning.

Finally, it is an object to provide such a method which employs only a very low concentration of a cryoprotectant additive which is nontoxic and can be administered to an animal along with a therapeutic protein.

SUMMARY OF THE INVENTION

The aforementioned objects are achieved by providing a method of protecting proteins such that their biological activity is preserved after freezing by exposing the protein to a carbohydrate and transition metal ion, and then freezing the protein. In preferred embodiments, the protein is exposed to 2 mM $Zn^{+2}$ and 50 to 100 mM concentration of a polyhydroxyl carbohydrate, such as trehalose, in an aqueous solution. By adding as little as a 25 mM concentration of polyhydroxyl carbohydrate with 2 mM $Zn^{+2}$ to the solution, the protein will retain much of its biological activity. It is usually not necessary to expose the protein to concentrations of polyhydroxyl carbohydrate any greater than about 25-100 mM, since on average, better than 90% retention of activity is observed even at these very low concentrations.

In some preferred embodiments, the pretreated, cryoprotected frozen protein is exposed to a vacuum at low temperature to dehydrate it in a process known as lyophilization. A therapeutically effective amount of a cryoprotected pharmaceutically useful protein, such as insulin, can be lyophilized and packaged for distribution to users of the protein, such as diabetics. Lyophilized proteins can be administered by simply rehydrating them and administering them to a user without removing the nontoxic carbohydrate and transition metal ion from the protein. In other embodiments, the protein could be dialyzed to remove the cryoprotectant additives, if desired.

In other embodiments, the protein and cryoprotectant are frozen and stored without loss of the protein's biological activity. Freezing the protein greatly extends its shelf life as compared to the shelf life of proteins which are simply refrigerated.

It has been found that divalent transition metal ions such as $Zn^{+2}$, $Cu^{+2}$, $Cd^{+2}$, $Ni^{+2}$, and $Co^{+2}$ work well in combination with polyhydroxyl carbohydrates to protect proteins from loss of biological activity due to freezing. This cryoprotective property is observed with even trace amounts of $Zn^{+2}$, for example, in less than 0.25 mM $ZnSO_4$ solution. The preferred concentrations of the transition metal ion are greater than 0.5 mM, more preferably greater than 1 mM, and most preferably about 1-2 mM concentration of transition metal ion.

In the presence of 2 mM transition metal ion, cryoprotection is observed with carbohydrates such as trehalose, maltose, lactose, sucrose, cellobiose, glucose, galactose, fructose, inositol, sorbitol, and glycerol.

BRIEF DESCRIPTION OF THE DRAWING

The drawing is a graph of percentage biological activity recovered by phosphofructokinase after freezing and thawing in the presence of varying concentrations of $ZnSO_4$ in a 100 mM aqueous solution of trehalose.

DETAILED DESCRIPTION

The term "soluble proteins" refers to proteins that are not bound in membranous structures such as cell membranes. The following data is limited to studies of soluble proteins since it is difficult to assess retention of biological activity of membrane-bound proteins. The presence of other biological structures in the cell membrane might affect findings of biological activity retained, hence the following data concern solely soluble proteins. The present invention is not limited, however, to cryoprotection of soluble proteins alone.

The enzyme phosphofructokinase (PFK) is used as one of the model proteins for the following cryoprotective studies. It was chosen for study since it is known to be ultrasensitive to cold and freezing, usually losing all biological activity after being frozen or lyophilized. Most other enzymes are also quite sensitive to loss of substantial biological activity after freezing and upon thawing.

The term "transition metal" is herein defined to include the elements appearing in Groups IB through VIIIB of the Periodic Table of the Elements.

EXAMPLE I

To prepare the PFK enzyme for freezing, PFK was dialyzed overnight against a 100 mM sodium phosphate buffer containing 5 mM dithiothreitol (pH 8.0). Then 20 microliters of the enzyme stock were added to 230 microliters of 2 mM $ZnSO_4$ and trehalose in aqueous solution (prepared in the above buffer) in polypropylene Eppendorf centrifuge tubes to give a final PFK concentration of approximately 0.025 mg/ml and a desired carbohydrate concentration of 100 mM. Duplicate assays of this enzyme-carbohydrate solution were made for PFK catalytic activity following the fructose 1,6-biphosphate-coupled procedure of Bock and Frieden, *J. Biol. Chem.*, 251:5630-5636 (1976). In this procedure, a Hitachi dual beam spectrophotometer Model 100-60 was used to measure disappearance of NADH, which absorbs at 340 nm. Alternately, an increase in absorbance at 340 nm was measured for NADP coupled assays. Then 150 microliters of the enzyme-carbohydrate solution were transferred to another Eppendorf centrifuge tube and frozen by immersion in liquid nitrogen for 30 seconds. The enzyme preparation was then thawed at room temperature and assayed immediately in the spectrophotometer for catalytic activity at 25° C. The values of percentage activity recovered were expressed as a percentage of the activity measured prior to freezing. A residual control sample (never frozen) was checked again for catalytic activity to ensure that it was stable during the experimental time period.

Using this procedure, PFK was found to retain 100% of its catalytic properties when treated in a 2 mM $ZnSO_4$ and 100 mM aqueous solution of trehalose prior to freezing.

EXAMPLE II

The procedure of Example I was repeated using the following concentrations of $ZnSO_4$ in the presence of 100 mM trehalose: 0.1 mM, 0.25 mM, 0.5 mM, 1.0 mM, and 1.5 mM. The precentage of enzymatic activity retained at each of these concentrations is shown in the drawing.

EXAMPLE III

The procedure of Example I was repeated using 100 mM trehalose and 2 mM concentration of the following salts instead of $ZnSO_4$ $Na_2SO_4$, $MgSO_4$, $MnSO_4$, $CuSO_4$, $NiCl_2$, $CoCl_2$, and $CdCl_2$. The percentage of enzymatic activity retained with each of these treatments is shown in Table 1.

TABLE 1

Protection of PFK from damage during freeze thawing: Influence of cation added in the presence of 100 mM trehalose

| Salt added (2 mM) | PERCENT ACTIVITY RECOVERED |
| --- | --- |
| None | 17.6 |
| $ZnSO_4$ | 100.9 |
| $MgSO_4$ | 18.7 |
| $MnSO_4$ | 22.7 |
| $CuSO_4$ | 66.9 |
| $CaCl_2$ | 20.7 |
| $CdCl_2$ | 33.4 |
| $NiCl_2$ | 76.8 |
| $CoCl_2$ | 79.0 |
| $Na_2SO_4$ | 17.7 |

Cryoprotection is seen to be enhanced by presence of a transition metal cation. Cations of the nontransition metals, Mg, Ca, Na, have little or no effects.

EXAMPLE IV

The enzyme PFK was prepared and frozen with trehalose as described in Example I, except no cation was added. After freezing, the PFK showed only minimal enzymatic activity. This data is also included in Table 1.

EXAMPLE V

The enzyme was prepared and frozen in the presence of a carbohydrate and 2 mM $ZnSO_4$ as described in Example I, except the enzyme was treated with a mM concentration of the reducing disaccharide maltose instead of the nonreducing trehalose. The procedure was repeated several times, each time substituting a 100 mM aqueous solution of a different one of the following disaccharide carbohydrates for trehalose: sucrose, lactose, and cellobiose.

Finally, the same procedure was performed except 100 mM solutions of monosaccharides such as inositol, glycerol, sorbitol, glucose, galactose, and fructose were substituted for the trehalose solution of Example I.

The precentage of biological activity recovered in each instance is shown in Table 2. For comparison, the percentage enzymatic activity retained by PFK following freezing and thawing in the presence of 100 mM carbohydrate with no zinc present is also given in Table 2.

TABLE 2

Protection of PFK from damage during freeze-thawing

| Carbohydrate Conc. (mM) | with 2 mM $ZnSO_4$ | | | with no $ZnSO_4$ | | |
| --- | --- | --- | --- | --- | --- | --- |
| | 25 | 50 | 100 | 25 | 50 | 100 |
| Trehalose | 91.9 | 100.0 | 100.9 | 0.0 | 16.8 | 19.7 |
| Maltose | 96.2 | 84.6 | 91.9 | 0.0 | 8.4 | 12.0 |
| Lactose | 89.4 | 93.9 | 54.4 | 1.5 | 9.7 | 15.8 |
| Sucrose | 87.1 | 93.0 | 94.3 | 0.0 | 9.0 | 12.7 |
| Cellobiose | 87.5 | 90.0 | 75.4 | 0.0 | 11.6 | 15.1 |
| Glucose | 77.4 | 97.3 | 103.6 | 0.0 | 2.4 | 16.9 |
| Galactose | 83.0 | 79.4 | 90.0 | 0.0 | 0.0 | 26.3 |
| Fructose | 92.2 | 74.1 | 97.6 | 0.0 | 0.0 | 14.9 |
| Inositol | 91.7 | 88.2 | 89.5 | 0.0 | 1.5 | 1.5 |
| Sorbitol | 93.2 | 100.0 | 100.9 | 0.0 | 1.5 | 16.3 |
| Glycerol | 73.7 | 84.6 | 102.5 | 0.0 | 0.0 | 11.6 |

Cryoprotection was greatly enhanced at all concentrations by the addition of 2 mM $ZnSO_4$.

EXAMPLE VI

The procedure of Example V was repeated by treating PFK with each of trehalose, sucrose, lactose, maltose, cellobiose, inositol, glycerol, glucose, galactose, fructose, and sorbitol, using the following concentrations of each: 25 mM and 50 mM. As a comparison, PFK was treated with each of the same carbohydrates at 25 mM and 50 mM, but no transition metal ion was added. The percentage of enzymatic activity retained by PFK following freezing and thawing during exposure to these varying concentrations of cryoprotectants is shown in Table 2.

EXAMPLE VII

PFK was again prepared and exposed to a 60 mM aqueous solution of trehalose with 0.32 mM $Zn^{+2}$. The procedure was followed as described in Example I up to the point of freezing the enzyme-carbohydrate solution, except a 0.1 M sodium phosphate buffer with 5 mM dithiothreitol was used. In this example, after the solution was frozen in liquid nitrogen, it was transferred under liquid nitrogen to a Labconco Model 8 Lyophilizer and lyophilized for 12 hours (at $-50°$ to $-70°$ C., and 5 to 10 microns of Hg vacuum). Upon removal from the freeze drying apparatus, the dry powder was redissolved in 150 microliters of distilled water containing 3.0 mM dithiothreitol and the final volume of the solution measured. This solution was assayed for PFK catalytic activity immediately and compared to control values. The percentage of PFK activity recovered was 75.4%.

EXAMPLE VIII

The cryoprotection and freeze-drying procedure of Example VII was repeated, except varying concentrations of maltose and glycerol solutions replaced the solution of trehalose used in Example VIII, and no metal ions were added. As a control, PFK was also simply freeze-dried without any carbohydrates or transition metal additives, and very little biological activity was recovered.

The concentrations of solutes and results of these procedures are summarized in the following Table 3:

TABLE 3

Protection of soluble protein (phosphofructokinase) during freeze-drying with no metal cations added

| Added Solute | Solute Concentration (mM) | PFK Activity (% Recovery) |
| --- | --- | --- |
| No Carbohydrate | 0 | 0 |
| Maltose | 20 | 30.6 |
| | 60 | 86.7 |

TABLE 3-continued

Protection of soluble protein
(phosphofructokinase) during freeze-drying
with no metal cations added

| Added Solute | Solute Concentration (mM) | PFK Activity (% Recovery) |
|---|---|---|
| Glycerol | 20 | 0 |
|  | 60 | 0 |
|  | 300 | 0 |

Glycerol alone (without transition metal cations shows no cryoprotection, while the data of Table 2 shows that glycerol in combination with 2 mM $Zn^{+2}$ preserves substantially all PFK activity at comparable concentrations. Maltose without zinc ion requires much higher concentrations of the carbohydrate to achieve comparable cryoprotection.

EXAMPLE IX

The freeze-drying procedure of Example VII was repeated, except 60 mM trehalose with 0.32 mM $Zn^{+2}$, 100 mM trehalose with 0.54 mM $Zn^{+2}$, and 300 mM trehalose with 1.62 mM $Zn^{+2}$ concentrations were used with PFK from rabbit muscle and lactate dehydrogenase (LDH) from rabbit muscle. To illustrate the cryogenic protection provided by trehalose in various buffers, PFK was freeze-dried in (a) 0.1 M sodium phosphate buffer with 5 mM dithiothreitol, pH 8.0 at 25° C.; (b) 0.02 M tricine-NaOH buffer with 5 mM dithiothreitol, pH 7.9 at 25° C.; and (c) 0.01 M sodium phosphate buffer with 5 mM dithiothreitol, pH 8.0 at 25° C. The results are shown in the following Table 4:

TABLE 4

Protection of proteins from damage during freeze-drying

PERCENT ACTIVITY RECOVERED

| PROTEIN | No Cryo-Protectant | 60 mM Trehalose with 0.32 mM $Zn^{+2}$ | 100 mM Trehalose with 0.54 mM $Zn^{+2}$ | 300 nM Trehalose with 1.62 mM $Zn^{+2}$ |
|---|---|---|---|---|
| PFK |  |  |  |  |
| (a) | 4.3 | 46.6 | 78.4 | 92.0 |
| (b) | 4.7 | 66.2 | 67.9 | 74.6 |
| (c) | 0.0 | 75.4 | — | — |
| LDH |  |  |  |  |
| (a) | 11.5 | 32.9 | 66.3 | 91.3 |
| (b) | 0.0 | 45.6 | 53.4 | 79.4 |

The effects of varying buffer solution concentration are seen to be minimal when freeze-drying PFK but more significant when freeze-drying LDH.

EXAMPLE X

To illustrate the usefulness of a $Zn^{+2}$-polyhydroxyl carbohydrate mixture as a cryoprotectant for proteins other than PFK during freeze-thawing, the freeze-thawing method of Example I was repeated using several other proteins at 60 mM, 100mM, and 300 mM concentrations of trehalose with $Zn^{+2}$ concentrations of 0.32 mM, 0.54 mM, and 1.62 mM, respectively. These proteins included lactate dehydrogenase (LDH) from rabbit muscle, pyruvate kinase (PK) from rabbit muscle, hexokinase (HK) from yeast, glutamate pyruvate transaminase (GPT) from pig heart, and aldolase (Aldo) from rabbit muscle. Lactate dehydrogenase was assayed for catalytic activity at 25° C. in a reaction mixture containing 2 mM sodium pyruvate, 0.15 mM NADH, 100 mM KCl and 80 mM Tris-HCl, pH 7.5. Pyruvate kinase was assayed in a reaction mixture containing 1 mM phosphoenolpyruvate, 5 mM ADP, 10 mM $MgSO_4$, 0.15 mM NADH, 15 units/ml LDH, 100 mM KCl and 80 mM Tris-HCl, pH 7.5. Hexokinase activity was measured in a reaction mixture consisting of 5 mM glucose, 3 mM ATP, 6 mM $MgCl_2$, 0.5 mM NADP, 0.5 units/ml glucose-6-phosphate dehydrogenase, 3 mM dithiothreitol, 50 mM imidazole, 50 mM Tris-HCl, pH 8.0. Aldolase was assayed in a reaction mixture containing 1.1 mM fructose-1,6-bisphosphate, 0.15 mM NADH, 20 micrograms triose phosphate isomerase, 50 micrograms glycerol-3-phosphate dehydrogenase, 3 mM dithiothreitol, 50 mM imidazole, 50 mM Tris-HCl, pH 8.0. Glutamate-pyruvate transaminase activity was analyzed using a reaction mixture containing 1.0 M alanine, 9.6 mM alpha-ketoglutarate, 0.15 mM NADH, 9 units/ml LDH, 50 mM sodium phosphate buffer, pH 7.5.

In the cases of NADH-coupled assays which consumed NADH, the decrease in absorbance was followed at 340 nm. For the NADP-coupled assay which produced NADP, the increase in absorbance was followed at 340 nm.

Percent of activity recovered by the proteins is shown in Table 5 below:

TABLE 5

Protection of proteins from damage during freeze-thawing

PERCENT ACTIVITY RECOVERED

| PROTEIN | 60 mM Trehalose with 0.32 mM $Zn^{+2}$ | 100 mM Trehalose with 0.54 mM $Zn^{+2}$ | 300 mM Trehalose with 1.62 mM $Zn^{+2}$ |
|---|---|---|---|
| LDH | 85.4 | 87.9 | 103.1 |
| PK | 93.5 | 94.7 | 105.0 |
| HK | 66.2 | 79.9 | 98.0 |
| GPT | 83.7 | 103.5 | 97.3 |
| Aldo. | 87.8 | 95.8 | 103.1 |

EXAMPLE XI

The freeze-thawing procedure of Example X was repeated, but the following carbohydrates were substituted for trehalose: maltose, glycerol, and sorbitol. No $Zn^{+2}$ or any other transition metal ion was added.

Percent activity recovered by the proteins is shown in Table 6 below:

TABLE 6

Protection of proteins from damage during freeze-thawing in presence of carbohydrate without transition metal cation

PERCENT ACTIVITY RECOVERED

| PROTEIN | 60 mM | | | 100 mM | | | 300 mM | | |
|---|---|---|---|---|---|---|---|---|---|
|  | M | G | S | M | G | S | M | G | S |
| LDH | 17.4 | 11.6 | 16.3 | 9.4 | 28.4 | 17.3 | 72.5 | 62.0 | 29.1 |
| PK | 29.2 | 43.0 | 31.2 | 39.4 | 60.0 | 34.2 | 79.9 | 75.1 | 49.0 |
| HK | 33.3 | 42.1 | 38.3 | 29.9 | 47.7 | 35.5 | 61.9 | 77.0 | 39.2 |
| GPT | 46.9 | 47.9 | 41.2 | 32.0 | 59.7 | 34.1 | 59.8 | 55.8 | 59.2 |
| Aldo. | 60.2 | 61.9 | 61.9 | 59.2 | 71.2 | 66.8 | 78.4 | 86.3 | 70.0 |

As a comparison, the freeze-thawing procedure was repeated with no transition metal ion or carbohydrate added. The results of this procedure are shown in Table 7:

TABLE 7

Percent Activity Recovered With No Carbohydrate or Divalent Metal Cation Added

| PROTEIN | PERCENT ACTIVITY RECOVERED |
|---|---|
| LDH | 0 |
| PK | 38.4 |
| HK | 40.6 |
| GPT | 18.6 |
| Aldo. | 51.4 |

EXAMPLE XII

Aldolase from rabbit muscle was exposed to 100 mM trehalose and 0.54 mM $Zn^{+2}$ and assayed in a reaction mixture containing 100 mM tricine and 100 mM citrate at pH 8.0. Freeze-thawing was performed as in Example I, and 93.1% of biological activity was recovered.

EXAMPLE XIII

Human insulin for treatment of diabetes is usually packaged in dosage units, with about 40 units per milligram of insulin. A 100 unit vial of human insulin such as that sold by Eli Lilly and Co. under the trademark HUMULIN would be prepared and exposed to 100 mM trehalose and 2 mM $Zn^{+2}$ as described in Example I. The insulin would then be frozen an stored in a freezer until ready for use, thereby prolonging the shelf life of the drug. A user would remove the insulin from the freezer and thaw it prior to use. The thawed insulin and trehalose/$Zn^{+2}$ would be injected into a user without removing the trehalose from solution.

EXAMPLE XIV

A 100 unit vial of human insulin would be obtained using known recombinant DNA techniques. The insulin would then be prepared and exposed to 100 mM trehalose and 2 mM $Zn^{+2}$ and lyophilized using the procedure of Example VII. The lyophilized insulin would then be stored in powdered form until ready for use. The user would then add enough sterilized water to the lyophilized preparation to obtain the unit concentration desired for the particular diabetic's condition.

EXAMPLE XV

The procedure of Examples XIII and XIV would be repeated, except the trehalose and $Zn^{+2}$ would be removed by dialysis from the insulin after thawing or rehydration and prior to injection.

EXAMPLE XVI

The procedure of Examples XIII or XIV would be repeated using therapeutically useful proteins and peptides other than insulin. Examples of such pharmaceutical proteins include interferon, beta-endorphin, lymphokines, interleukins, peptide growth factors, and numerous peptide hormones. Examples of the peptide hormones that could be preserved by this method include vasopressin, transferrin, relaxin, prolactin, and growth hormone.

EXAMPLE XVII

Artificial red blood cells (RBC) for transfusion could be prepared by encapsulating human hemoglobin in liposomes. The liposome and encapsulated hemoglobin would be exposed to 100 mM trehalose and 2 mM $ZnSO_4$ as described in Example I. The liposome and hemoglobin could then be frozen (as in Example I) or lyophilized (as in Example VII) to preserve and store the artificial RBC. The artificial RBC would then be thawed or rehydrated when needed for a transfusion without loss of biological activity of the hemoglobin. The trehalose will cryogenically protect the liposome, as illustrated by Crowe's work discussed in the Background. The protein hemoglobin will also be cryogenically protected by the trehalose and zinc, as illustrated by the present work. Journal articles illustrating preparation of artificial RBCs for liposomes include Yuasa et al., *Journal of Pharmacobio-Dynamics*, Vol. 8, No. 1 at page 17 (1985); Dimitrov, *International Journal of Microcirculation-Clinical and Experimental*, Vol. 3, No. 3-4, page 387 (1984); Hunt et al., *Science*, No. 230, pages 1165-1168 (1985).

The foregoing Examples I-XVII illustrate specific methods of cryoprotection for a variety of proteins. Generally, it would be more desirable to use a nonreducing carbohydrate such as trehalose to avoid the protein browning effects of reducing carbohydrates such as maltose. Protein browning can cause a stored protein to turn brown after prolonged exposure and lose its biological activity.

Nonreducing carbohydrates are those not having a free carbonyl group and include trehalose, sucrose, inositol, sorbitol, and glycerol. Reducing carbohydrates do have a free carbonyl group and include maltose, lactose, cellobiose, glucose, galactose, and fructose.

Having illustrated and described the principles of the invention in a preferred embodiment, it should be apparent to those skilled in the art that the invention can be modified without departing from such principles. We claim all modifications coming within the spirit and scope of the following claims.

We claim:

1. A method of inhibiting loss of biological activity due to freezing of artificial red blood cells comprised of a liposome encapsulating hemoglobin, the method comprising the steps of:

exposing the artificial red blood cell to effective amounts of a cryoprotectant comprising trehalose and a transition metal ion, said effective amounts being sufficient to inhibit loss of biological activity due to freezing; and freezing the artificial red blood cell.

2. A composition comprising the product of claim 1.

3. The method of claim 1 further comprising the step of lyophilizing the artificial red blood cell.

4. A composition comprising the product of claim 3.

* * * * *